United States Patent
Ledergerber

(10) Patent No.: US 8,765,039 B1
(45) Date of Patent: Jul. 1, 2014

(54) IMPLANTABLE MICRO-TEXTURED SCAR INDUCING EPTFE STRUCTURES

(76) Inventor: Walter J. Ledergerber, Dublin, CA (US)

(*) Notice: Subject to any disclaimer, the term of this patent is extended or adjusted under 35 U.S.C. 154(b) by 331 days.

(21) Appl. No.: 13/275,018

(22) Filed: Oct. 17, 2011

Related U.S. Application Data

(60) Provisional application No. 61/408,453, filed on Oct. 29, 2010.

(51) Int. Cl.
  *B29C 65/02* (2006.01)
  *B29C 59/02* (2006.01)
  *A61F 2/06* (2013.01)

(52) U.S. Cl.
  CPC ............ *B29C 59/021* (2013.01); *B29C 59/02* (2013.01); *A61F 2/06* (2013.01); *A61F 2/064* (2013.01)
  USPC ....................................... 264/162; 623/23.76

(58) Field of Classification Search
  CPC ......... B29C 59/02; B29C 59/021; A61F 2/06; A61F 2/064
  USPC ....................................... 623/23.76; 264/162
  See application file for complete search history.

(56) References Cited

U.S. PATENT DOCUMENTS

| | | | | |
|---|---|---|---|---|
| 4,187,390 A * | 2/1980 | Gore | ................. | 174/102 R |
| 5,462,781 A * | 10/1995 | Zukowski | ............. | 428/36.1 |
| 5,628,786 A * | 5/1997 | Banas et al. | ............. | 623/1.13 |
| 6,016,848 A * | 1/2000 | Egres, Jr. | ............. | 138/137 |
| 6,187,039 B1 * | 2/2001 | Hiles et al. | ............. | 623/1.44 |

* cited by examiner

*Primary Examiner* — Galen Hauth
(74) *Attorney, Agent, or Firm* — David B. Murphy; O'Melveny & Myers LLP

(57) ABSTRACT

Bio-implantable textured tubular and sheet structures of unsintered ePTFE are described. Such micro-textured structures stimulate robust development of beneficial bio-integrative scar attachment to adnexal soft tissues. Methods for texturing one side of an un-sintered extruded ePTFE tube or sheet are also described. A select length of tubing of any thickness or diameter is applied over a matching mandrel and adhesively stabilized thereon by applying intense suction. The texture is made by "RIGDA tooling" into the wall thickness of the material and by removing undesired material by distraction and avulsion tooling and methods assisted by vibration, leaving intact the finished product. Disclosed is an implantable, non-attached, enveloping, conforming and supportive drainage cover for breast and other soft implants. The drainage cover has numerous through and through cut lucencies which allow for liberal ingress and egress of interstitial biologic fluids enabling efficient drainage postoperatively, especially under the influence of active wound suction.

6 Claims, 8 Drawing Sheets

IMPLANTABLE MICRO-TEXTURED SCAR INDUCING EPTFE STRUCTURES

CROSS-REFERENCE TO RELATED APPLICATION

This application claims priority to U.S. Provisional Patent Application No. 61/408,453, filed Oct. 29, 2010, the contents of which are incorporated by reference herein in their entirety as if fully set forth herein.

RELATED APPLICATIONS STATEMENT

This application is related in subject matter to my prior patents including: U.S. Pat. No. 4,955,907 (Apr. 11, 1990), U.S. Pat. No. 5,282,856 (Feb. 1, 1994), U.S. Pat. No. 5,462,781 (Oct. 31, 1995), U.S. Pat. No. 5,653,755 (Aug. 5, 1997), U.S. Pat. No. 5,779,734 (Jul. 14, 1998), U.S. Pat. No. 4,187,390 (Feb. 5, 1980), U.S. Pat. No. 6,921,418 (Jul. 26, 2005), U.S. Pat. No. 7,041,127 (May 9, 2006), and U.S. Pat. No. 7,273,493 (Sep. 25, 2007), which are hereby expressly incorporated by reference in their entirety. No claim of priority is made to any of these prior patents.

FIELD OF THE INVENTION

The present inventions related to improved biocompatible implants, and methods for their manufacture, for use in the body. In particular, the inventions relate to improved biocompatible implants having enhanced tissue in-growth properties. In another aspect, the present invention relates to an implantable enabling device for breast augmentative and reconstructive surgery in particular and to surgical wound drainage care in general.

BACKGROUND OF THE INVENTION

A textured dual-sided sheet of ePTFE, as in my U.S. Pat. Nos. 5,282,856 and 6,921,418, has multiple uses as an implant in surgical reconstruction of the body. It has applicability as a fitted covering for space-occupying implants that require isolation and stabilization such as implanted infusion pumps, orthopedic devices, electronic devices such as defibrillators, glucose meters, pacemakers, and others. It also finds applicability as a hernia repair material, as a safe hypoallergenic dura mater replacement material, as supportive coverings for soft organs such as kidney, pancreas, liver or spleen, for example. It is also useful as a protective support and drainage cover for breast and other soft implants. Additionally, it is useful as a repair material for wall of thorax, ruptured diaphragm, pericardium, and so forth.

Used as an implanted covering, the textured dual-sided ePTFE sheet structure is very useful for its ability to induce bio-integrative scar on its textured surface, thus enabling it to become quickly and permanently attached to adjacent bodily structures. A textured dual-sided ePTFE tubular structure is another useful implantable structure that benefits from the ability to bio-integrate with the body. Drugs, transplanted live tissues in their nutrient media including: pancreatic beta cells, bone marrow, stem cells, and others contained within such a textured sheet or tubular repository structure can serve as in situ reservoirs upon healing.

Bio-integration implies an intense adherence between an implanted material and the body, which can help defeat potential complications of surgery such as de-lamination, dehiscence and seroma fluid accumulation. The avidity of bio-integrative scar attachment is principally characterized as the amount of force required to physically separate the tubular ePTFE structure from attached soft tissue under standardized test conditions.

Whereas smooth ePTFE surfaces with porosities in the 1-2 micron range are used to prevent adherence to bodily structures, the purpose of micro-textured ePTFE is to do the opposite—to induce targeted bio-integrative scar and adherence. Creating both smooth and micro-textured surfaces on the same implantable ePTFE structure is a manufacturing challenge. Crafting both surfaces on a tubular ePTFE structure adds another degree of complexity. In order to attract fibroblasts, textured ePTFE surfaces must be free of oxidized by-products and other surface contaminants such as manufacturing debris, glazing, or extrusion impressions.

According to Goldfarb (U.S. Pat. No. 6,436,135), by providing the appropriate wall thickness of the textured tubular structure, as well as by creating through and through holes or slits of optimal diameter and density, a highly desirable neo-intima cell layer can be encouraged and supported with capillary in-growth into the lumen. It discloses a prosthetic vascular device formed from a small bore tube of polytetrafluoroethylene which has been heated, expanded and sintered so as to have a microscopic superstructure of uniformly distributed nodes interconnected by fibrils and characterized by: (a) an average internodular distance which is (i) large enough to allow transmural migration of typical red cells and fibroblast, and (ii) small enough to inhibit both transmural blood flow at normal pressures and excessive tissue ingrowth; and (b) an average wall thickness which is (i) small enough to provide proper mechanical conformity to adjacent cardiovascular structures, and (ii) large enough, when taken in conjunction with the associated internodular distance, to prevent leakage and excess tissue ingrowth, to allow free and uniform transmural nutrient flow, and to assure mechanical strength and ease of implantation.

According to Zukowski (U.S. Pat. No. 5,462,781) entitled "Surface Modified Porous Expanded Polytetrafluoroethylene and Process for Making", an implantable porous expanded polytetrafluoroethylene material has a microstructure of nodes interconnected by fibrils and the surface of the material has been modified by the removal of fibrils from the surface. The surface has the appearance of freestanding node portions not interconnected by fibrils but rather having open valleys disposed between the freestanding node portions. Unmodified material beneath the surface maintains the original microstructure of nodes interconnected by fibrils. The modification is preferably done by exposing the surface to radio frequency gas plasma discharge with a reactive etching gas for a lengthy amount of time such as about ten minutes. The depth of fibril removal from the surface is substantially a function of the duration and amount of energy applied to the surface.

According to Gore (U.S. Pat. No. 4,187,390) entitled "Porous products and process therefore", a tetrafluoroethylene polymer in a porous form has an amorphous content exceeding about 5% and has a micro-structure characterized by nodes interconnected by fibrils. The material is said to have high porosity and high strength. Shaped articles such as films, tubes, rods, and continuous filaments are contemplated. Laminations can be employed and impregnation and bonding can be used.

Historically, severe scar contracture around a silicone breast implant would harden and deform the entire breast, with consequences for both patient and surgeon. Multiple causes of scar contracture have been identified, including a ready supply of seroma fluid containing collagen monomers, cellular debris, mediators of inflammation due to surgical injury, physical abrasion and exposure to allergenic materials like silicone gel, and wound contaminants. In the case of wounds containing soft implants, seroma fluid containing collagen monomers and admixed mediators of inflammation are problematic because such a combination promotes additive layers of scar. A large amount of fluid permits an implant to float in the wound space and allows for mechanical abrasion as it makes repeated abrasive contact with surrounding soft tissues, and thus can become a serious complication of surgery. So-called developing "capsular scar contractures" become thicker and more dense and grossly distort an implant and surrounding breast tissue.

Over time, a number of partial solutions to the problem of scar contractures have been tried including: (1) more cohesive gel fillers for implants which are less likely to be allergenic and more likely to retain implant shape, (2) sub-muscular rather than sub-glandular placement of implants, (3) non-allergenic fillers such as normal saline, (4) pressure adaptive implants, (5) fastidious surgical dissection technique with frequent wound irrigation and suction, (6) use of corticosteroid injections into surrounding soft tissues, and (7) topography-modifying implant surfaces, as well as others.

However, significant esthetic problems of sub-optimal implant position, implant deformation and hardness remain for some patients, often necessitating re-operation plus installing a new set of implants. Implant motion and abrasion injury at the interface with soft tissue results in accumulation of seroma fluid in the wound. Such seroma fluid accumulation which contains cellular debris, mediators of inflammation, fibroblasts and collagen, remains an un-solved problem requiring a solution. Because it can persist for a prolonged period of time in a wound space as an inflammatory material, it promotes the development of multiple layers of capsular scar. Such capsular scar can then undergo severe contraction to deform the entire breast.

SUMMARY OF THE INVENTION

In one aspect, the present invention is an "Implantable Textured Tubular ePTFE Structure". The Method of Manufacture and preferred RIGDA Tooling for making this textured tubular device are described and also claimed.

New and improved bio-implantable textured tubular and sheet structures of un-sintered ePTFE are described. Such micro-textured structures stimulate the robust development of beneficial bio-integrative scar attachment to adnexal soft tissues. When confronted with an inviting ePTFE surface structure, fibroblasts are attracted to it and insinuate themselves by diapedesis into available interstices and secrete liquid collagen monomers within the "forest" of variegated villous remnants of substrate ePTFE. Such deposited monomers of collagen, attract more fibroblasts and are substantively in non-parallel alignment due to the great complexity of the spaces into which they are secreted. Deposited monomers of collagen subsequently "cement in place" by undergoing polymerization and become deep anchorages for maturing scar tissue. Angiogenesis rapidly develops within such scar matrix accelerating its development. Foundational scar adheres to a very complex pristine crystalline surface with unusual tenacity and thus bio-integrates with the ePTFE implant. The greater such surface area and the greater the complexity of such insinuating scar, the more avid the adherence establishing bio-integration. Trials of a variety of textures have shown that optimal fibroblast in-growth, resulting in optimal bio-integrative scar development, is a function of a dense pristine and complex crystalline topology featuring very numerous tattered and shredded surface villi.

In one aspect of the invention, an implantable tube for use in a body is provided. The tube is an extruded ePTFE tube with a first inner surface and a second outer surface. The tube has a thickness dimension between the first inner surface and the second outer surface. The second outer surface is textured to promote body tissue bio-integration into the second surface. Preferably, the second outer surface is textured by the process of releasably affixing the first inner surface to a work surface, contacting an active rotary gouge to the second outer surface to remove material from the tube, at least including gouging material in the thickness dimension from the second surface toward the first surface, thereby separating the gouged material from the tube, thereby forming an irregularly configured second outer surface, the outer surface having resultant irregular voids, and removing the gouged material textured second surface. The gouged or avulsed material reveals a pristine avulsed crystalline exposed ePTFE surface. Textured surface voids of 2 to 20 microns in depth are preferred. Textured surface voids of at least 15 microns, even deeper than 20 microns, are also preferred.

New and improved methods for texturing one side of an un-sintered extruded ePTFE tube or sheet are also described. A select length of tubing of any thickness or diameter is applied over a matching mandrel and adhesively stabilized thereon by applying sufficient suction to hold the tube while being textured. The texture is made by "RIGDA tooling" into the wall thickness of the material and by removing undesired material by distraction and avulsion tooling and methods assisted by vibration, leaving intact the finished product. The RIGDA tooling instrument may be a modified burr made of tool steel, a RIGDA disc made of ceramic, diamond grit, or other suitable particulate abrasive material. The entire selected surface may be textured or a complex texture pattern may be applied. The ePTFE tubing as well as sheets may be engineered utilizing any length, wall thickness, node and fibril structure, texture, voids, laminations or other features to suit. Sheets can be micro-textured and otherwise structured to enhance their use as a way to protect and support bodily tissues as well as in drainage of seroma fluids. The applied micro-texture stimulates bio-integrative scar when implanted.

In one implementation of the methods for texturizing an implantable tube or other structure, a surface being textured by the process uses the steps of providing a mandrel sized to receive the inner surface of the tube, the mandrel having a plurality of holes to couple the inner surface of the tube to a vacuum space. The mandrel and tube are releasably affixed by application of a vacuum to the vacuum space. An active rotary gouge contacts the second outer surface to remove material from the tube, at least including gouging material in the thickness dimension from the second surface toward the first surface, thereby separating the gouged material from the tube, thus forming an irregularly configured second outer surface, the outer surface having resultant irregular voids. Next, the gouged material is removed from the textured second surface. Preferably, the rotary gouge and mandrel are moved relative to one another. In one aspect, the rotary gouge may be moved parallel to the axis of the tube. Alternately, the rotary gouge may be moved at any other angle relative to the axis of the tube, including perpendicular to the axis of the tube. Discontinuing application of the vacuum permits removal of the texturized tube from the mandrel.

The permanent fixation of such textured ePTFE structures in the body is facilitated by the fact that favorable highly complex pristine crystalline topology induces rapid growth of scar tissue into the micro-textured surface and thus makes bio-integration possible. Preferably, the bio-integration is adapted to occur at least 15 microns in the thickness direction from the second outer surface.

Also, bonding and laminating will be greatly facilitated by RIGDA Tooling creation of a micro-texture surface on ePTFE tubing as well as other like structures. Adhesives bond much more successfully to micro-textured ePTFE surfaces, representing greatly increased surface areas. RIGDA Tooling used as taught herein will likely be a useful method for configuring many new medical devices.

Multiple manufacturing options can be brought to bear on textured tubular ePTFE structure design. Generic textured tubular ePTFE can be manufactured in a large variety of porosities manifested as node and fibril micro-structures, in extruded stock diameters, thicknesses and lengths. It can be customized for a variety of uses by heat welding, bonding, laminating, by tapering the tube in the lengthwise dimension, by cutting through-and-through holes or slits in the wall of these tubes, and utilizing other manufacturing techniques. Further, it can be configured to serve as a repository for drugs which can be introduced into the micro-structural voids within the tubular material by applying inert gas pressure externally. The structure so infused with drug may then be freeze-dried to extend the shelf life of the device/drug combination. The tube can additionally be inverted on itself so that the texture is manifested on its inner surface.

The desired texture which is created into the thickness dimension of the extruded ePTFE tube can be customized to satisfy unique engineering specifications (see FIGS. 3 and 4 etc.), particularly if the intended use is as a blood vessel prosthesis or graft.

The present invention is a soft supportive drainage cover for implants that is improved by at least two features: (1) the bio-integrative character of the texture that is applied to the outward facing side of a thin un-sintered ePTFE sheet, with the opposite side being smooth, plus (2) a high number of lucencies (used herein in the context of holes, slits, or other passageways) cut through the drainage cover to permit interstitial fluid to enter and to be drained effectively, and to permit the cover to adaptively conform to a given implant shape.

In yet another aspect of the inventions, an implantable, non-attached, enveloping, conforming and supportive drainage cover for breast and other soft implants is provided. It is an improvement over prior art in that it helps deal with implant motion, seroma fluid accumulation, and helps to minimize excess scar in a wound. It is a bi-lobed ePTFE sheet-like cover that has two distinct surfaces. It has a unique bio-integrative texture on the side directly facing the body soft tissues, that is—away from the implant itself, and a smooth surface on the opposite side facing toward the implant. The micro-texture which induces scar attachment to soft tissues is made by a unique RIGDA Process. The drainage cover has numerous through and through cut lucencies which allow for liberal ingress and egress of interstitial biologic fluids enabling efficient drainage postoperatively, especially under the influence of active wound suction. Furthermore, it severely limits shear motion at the soft tissue-drainage cover interface acutely, provides for long-term structural support of bio-integrated breast tissue, and protects against capsular contracture.

The invented drainage cover is a significant advance over prior art because it confronts the problems of the prior art directly. The micro-textured multi-lucent drainage cover described herein enables breast tissue to be sucked down into intimate contact with the drainage cover. This enables bio-integration of the cover thus minimizing shear motion of the implant, and also allows for the effective drainage of seroma fluid. The reduction of motion at the soft tissue-breast prosthesis interface, along with improved drainage of seroma fluid are significant solutions to some of the aforementioned problems.

In one implementation of the seroma drainage device for use in a body, a first ePTFE sheet has a first surface and a second surface. The second surface is textured to promote body tissue bio-integration into the second surface. Preferably, the second outer surface is textured by the process of releasably affixing the first inner surface to a work surface, contacting an active rotary gouge to the second outer surface to remove material from the tube, at least including gouging material in the thickness dimension from the second surface toward the first surface, thereby separating the gouged material from the tube, thereby forming an irregularly configured second outer surface, the outer surface having resultant irregular voids, and removing the gouged material textured second surface. A plurality of lucencies are disposed between the first surface and the second surface, the lucencies being adapted to permit the flow of fluids within the body from the first surface to the second surface.

Seroma fluid normally accumulates in a surgical wound as the result of tissue injury and contains many inflammatory mediator substances, collagen monomers and blood components. If not expeditiously eliminated, seroma fluid can result in chronic abrasion, more inflammation, excessive scar deposition, more seroma production and deforming capsular contractures.

External pressure dressings and closed suction are used to initiate peri-implant wound drainage after surgery. However, the surgeon needs a way to prolong the efficient suctioning of the peri-implant space until the wound is more advanced in the healing process. Blood clot can obstruct the suction system and cause a drain to fail. Wound suctioning needs to begin early and to be sustained for a period of time. The lucencies created in the invented cover help to mobilize seroma fluid quickly and help to sustain suction allowing for sufficient contact time between soft tissues and the cover to bio-integrate properly. Friction and abrasion are thereby minimized and breast tissue is supported.

The described cover adheres to enveloping breast tissue by bio-integrating with it. A pristine crystalline and complex ePTFE surface is a requirement for the texture that serves to induce "bio-integrative scar". The bio-integrative process begins when fibroblasts are attracted to the pristine complex crystalline surface whose method of texture manufacture is described earlier and pertains herein again in full. Insinuated fibroblasts get situated within the textured surface and secrete collagen monomers which then polymerize.

As polymerization of collagen proceeds, scar is incorporated into and onto the complex topography of the hyper-convoluted surface. It adheres intensely to the ePTFE sheet and thereby grossly reduces or eliminates shear motion at the soft tissue interface with the cover.

DETAILED DESCRIPTION

Figure 1:
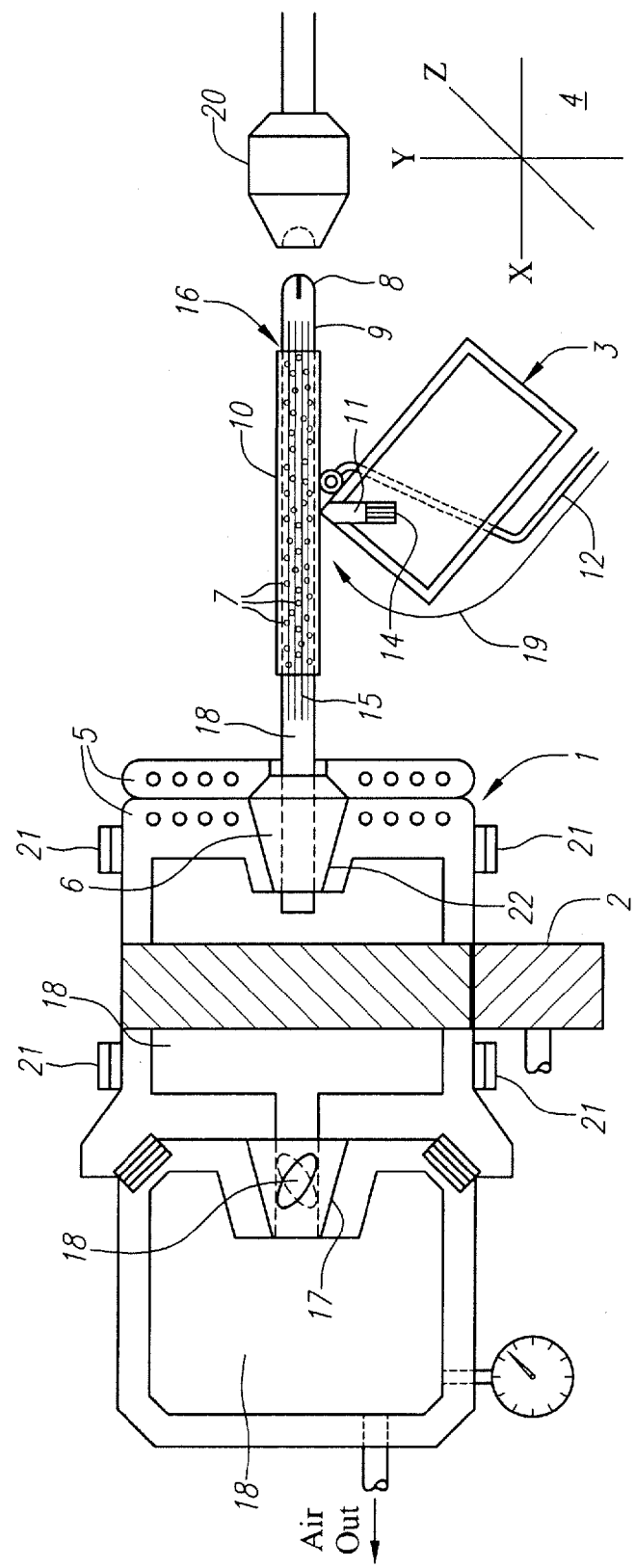
FIG. 1 is a semi-schematic top view of a preferred embodiment of the preferred apparatus for creating the texture into the thickness dimension of dual-sided tubular ePTFE.
Figure 2:
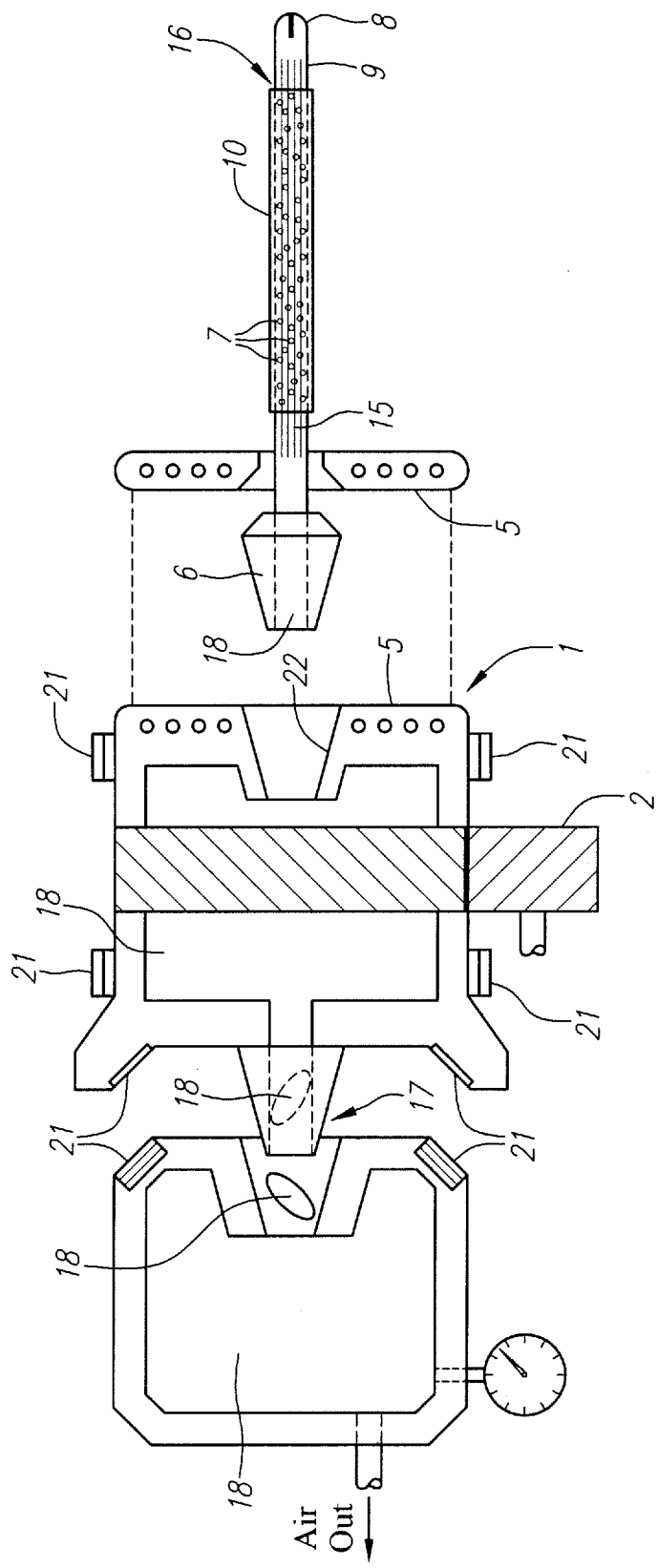
FIG. 2 clarifies relational detail in an exploded magnified semi-schematic top view of the spindle-mandrel apparatus of the preferred embodiment depicted in FIG. 1.

Referring to FIGS. 1 and 2, the hollow spindle/mandrel assembly 1 is mounted on a lathe which has a computer-controlled variable speed drive 2 and including "forward and reverse". Programmable rotating and reciprocating motions of the lathe advance the spindle/mandrel assembly 1 into position with respect to the compound motion "RIGDA Tool Assembly" 3, which is made to transition along three axes 4 independently. All feed motions are made programmable on the machine. A vacuum source is fitted to the machine. It should be noted that FIGS. 1 and 2 are concept drawings and thus are semi-schematic. As would be appreciated by a person skilled in the art, actual manufacturing drawings very likely would appear different.

The spindle-mandrel 1 is comprised of a solid high grade stainless steel tank, other structural materials, an adaptive coupling consisting of an integrated hollow conical electromagnetically actuated, and keyed socket chuck 5 which receives the standard precision fit stainless steel conical bases of interchangeable mandrels. 6 Mandrel portions with conical bases are essentially tubular elements designed to adhere to ePTFE substrate material.

Mandrels may be manufactured in any length and diameter to suit particular applications. The stainless steel tubular portion of each mandrel is multiply perforated 7 by "e.d.m." ("electrical discharge machined") or "laser-drilled" holes which permit vacuum-adherence stabilization of tubular ePTFE mounted thereon. The perforated end portion of the mandrel is made blunt and sealed by swaging and welding 8 or equivalent methods.

A segment of extruded tubular ePTFE is mounted on the selected mandrel manually in a "clean room" and affixed thereto by applying a vacuum preferably in an amount sufficient to hold the work piece in place during the texturizing operation, most preferably an intense vacuum through the mandrel 9. The programmed RIGDA tool creation of the micro-texture (see below) into the thickness dimension of the tubing wall 10 then proceeds with vacuum adherence stabilization of the tubular ePTFE substrate and with all requisite motions of the RIGDA tool. In one preferred embodiment, "RIGDA-tooling" is performed by at least one RIGDA tool 11 rotating at approximately 2,000-6,000 rpm with the proximity and attitude of the selected RIGDA tool under micrometer adjustment control 14.

Vacuum adherence is achieved by collapsing the space 16 between the ePTFE tubing substrate and the perforated hollow mandrel. Vacuum is applied through the rotating aspiration coupling 17 located at the non-mandrel end, with the intensity of vacuum automatically controlled and brought to bear at the perforated portion of the mandrel. Vacuum space 18 is continuous through the entire spindle-mandrel. As applied via perforations through mandrel 7, the vacuum is made sufficiently intense so as to optimize the purchase caused by the edges of those perforations acting on ePTFE tubing, thereby firmly holding the tubing concentrically on the mandrel to ensure that there be no slippage whatsoever.

The tubular portion of the mandrel may additionally be splined 15 to assist in preventing slippage. The porous nature of the ePTFE substrate will allow for spontaneous gradual loss of vacuum as the—"rotary-impaling-gouging-distracting—avulsing—RIGDA process" takes place, therefore it is highly desirable to automatically re-establish sufficient vacuum to maintain good adherence.

Particulate ePTFE is scavenged by a dedicated vacuum system. Engineering specifications dictate relative motion of spindle-mandrel assembly 1, and electrically powered RIGDA Tool assembly 3. Pressurized nitrogen gas 19 is used to unclog RIGDA tools of ePTFE substrate chaff as well as to cool the tooling. Texture and surface topology will vary with selected "rotary tooling speed", tube wall thickness, tooling gouge design, angle and depth of tooling, substrate thickness, node and fibril micro-structure, and other variables. There will be a direct correlation between friction created by tooling action and the texture of the created micro-villi.

The optimal textured surface enabling bio-integration is achieved when the featured "RIGDA tooling process" applied to substrate tubular ePTFE material results in a micro-texture that is crystalline and pristine in quality and structurally sufficiently complex so that fibroblasts are induced to move into and onto the prepared surface. Such a surface topology consists of a complex of exposed tattered-frayed crystalline villous structural remnants of ePTFE and spatial voids which are very numerous in the 2.0-20.0 micron range 13. The larger such complex pristine surface area is, the greater the adherence of attracted fibroblasts and ultimately bio-integrative scar.

Removal of finished product is assisted by complete reversal of vacuum followed by switching off electrical current in the electromagnetic socket chuck lock 5.

Figure 6:
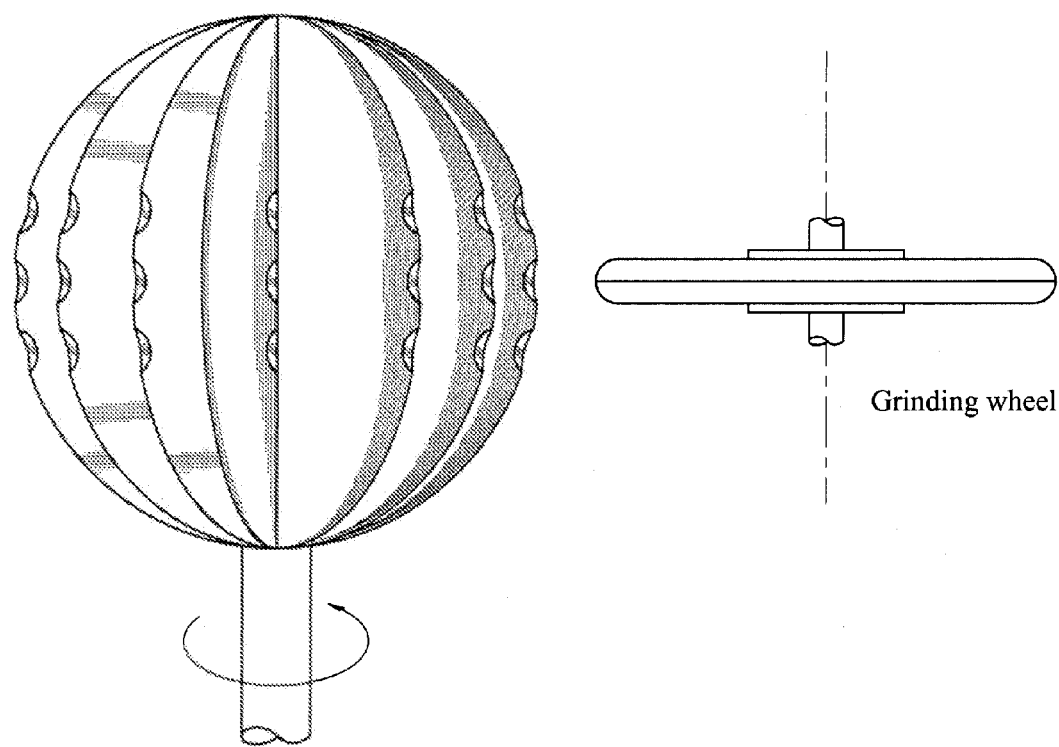
FIG. 6 depicts a prototypical preferred embodiment "Rotary Impaling, Gouging, Distracting, Avulsing Tool"—or "RIGDA Tool".

The "RIGDA TOOLING process" requires the introduction of an active rotary gouge (see FIG. 6) which gets aggressive purchase on/into the ePTFE material by "impaling" and "gouging" it. Upon "applying high torque rotary force", there is efficient "tearing" and "distracting" of the material at the crystalline level which continues until there is sudden "release-avulsion" of a variable amount of base material—leaving an irregularly configured remnant of substrate material and resultant irregular void. As shown in FIG. 6, multiple, such as 10 or more, vertical cutting teeth are provided. Each tooth projects outward from the center of the tool. A common shaft connects to the drive. Preferably, the teeth include gouges or divots to aid in the RIGDA process. Optionally, a grinding wheel may be used to form the gouge or divots.

Tooling furrow pattern, depth of tooling process, and substrate thickness are engineering specifications developed particularly for a given product. The dynamic nature of the RIGDA tooling process results in an "additional component of vibration inherent in the process due to sudden release of the tooling followed by the abrupt re-capture of additional substrate", resulting in ever greater variability of shape and length of shredded remnant villi and therefore of overall surface texture. FIGS. 3 A to E show optional patterns, such as (A) a cross-hatch, (B) parallel diagonal stripes, (C) complex hexagons or portions thereof, (D) linear stripes parallel to the axis of the tube, and (E) cross-hatched with interpositioned regions.

Figure 3A:
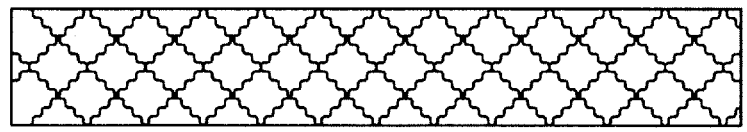
FIGS. 3A-D depict examples of furrow patterns of texture that can be created into the wall thickness of an ePTFE tubular structure with the apparatus in FIGS. 1 and 2.
Figure 3B:
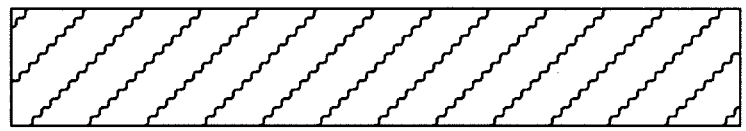
Figure 3C:
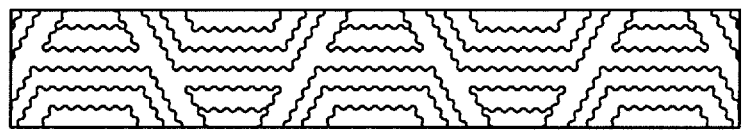
Figure 3D:
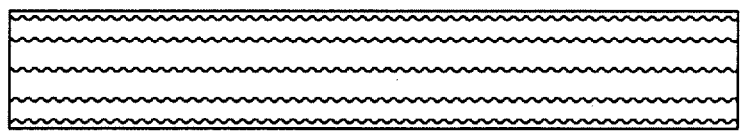
Figure 3E:
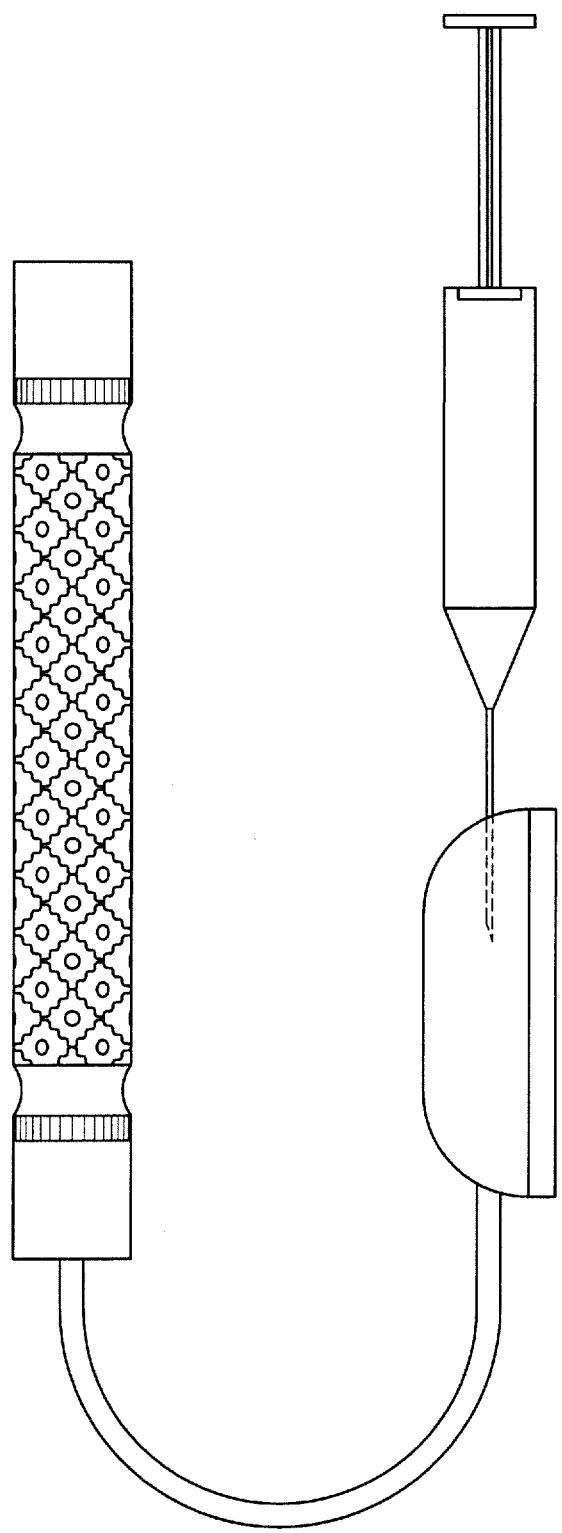
FIG. 3E depicts a textured tubular repository which may be used for localizing donor cells, radioactive isotope labeled drugs or other materials to internal bodily structures.

FIG. 3E depicts a textured tubular repository which may be used for localizing donor cells, radioactive isotope labeled drugs or other materials to internal bodily structures including organs such as the liver, lung, parietal pleura, spleen, pancreas, intestines, pelvic floor, retroperitoneal space, bone marrow and others. Minimal incision endoscopic techniques may be utilized. When implanted adjacent to targeted tissues that require a substantial drug treatment over time, a textured tubular repository may be configured to have a subcutaneous injection reservoir connected by a tube which would allow for substantive periodic loading of a drug followed by prolonged drug delivery directly into the tissue where it is needed.

In the wake of the micro-texture-creating RIGDA tooling process the predominant visible and palpable disposition of the substrate ePTFE is that of irregular exposed pristine crystalline villous remnants surrounded by a very complex physical space. On gross examination, the resultant white tooling furrow course resembles a soft plowed furrow in a farmer's field. Together, the cited "texture-creating RIGDA tooling actions" create the quality topology which stimulates the in-growth of fibroblasts.

Figure 5A:
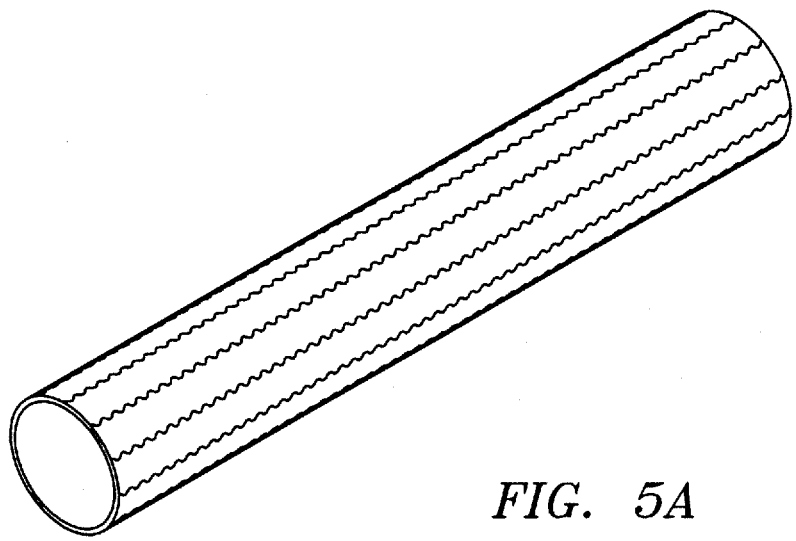
FIGS. 5A and 5B depict texture applied both internal and external to a textured tubular ePTFE repository.
Figure 5B:
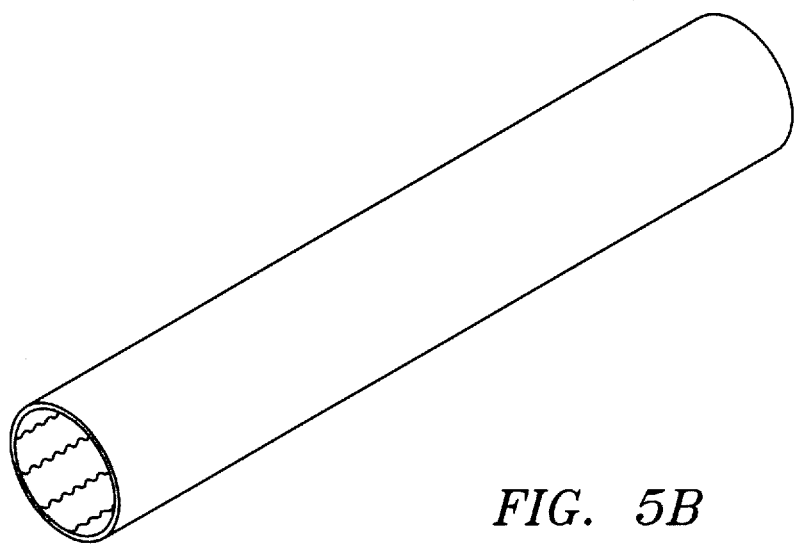

Real-time and delayed inspection of the manufacturing process is enabled by a video imaging system which provides for quality control documentation of enlarged images 13. Two basic versions of textured tubing may be made: "texture-out" and "texture-in" (FIGS. 5A and B). Simple inversion through the length of the tube segment is required after the RIGDA tooling process is complete.

Figure 4A:
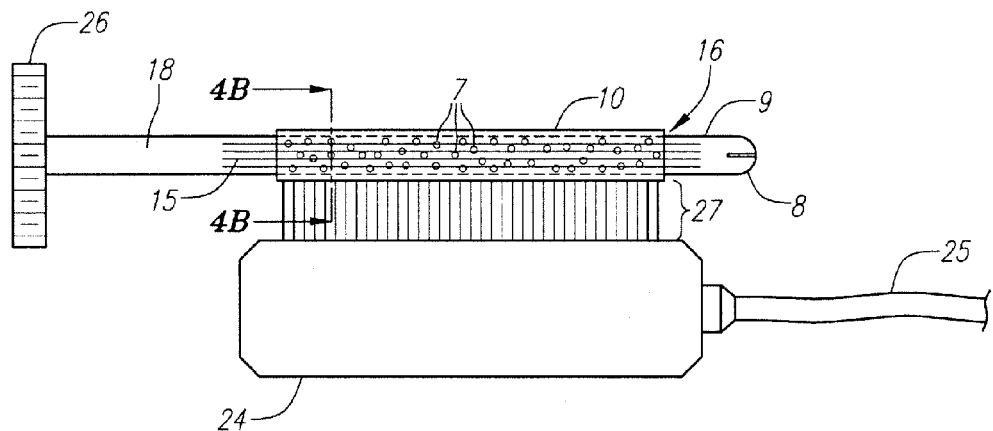
FIGS. 4A and 4B depict a prototypical scheme for efficient laser cutting of access holes through the wall of textured tubing.
Figure 4B:
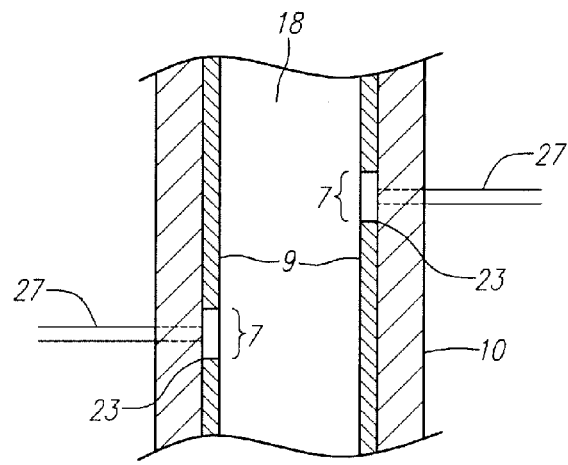

The following identifies particular components of the system: the spindle—mandrel Assembly 1; Vacuum Pump and Rotating Spindle-Mandrel are joined at "Floating Aspiration Coupling" 17; Highly polished surfaces, Teflon and Teflon Paste Bearings and Bushings utilized, Variable Speed Drive 2, Compound RIGDA Tooling Assembly 3 with electrical motor drives for tools, Micrometer Adjustable Control 14 of RIGDA Tool Position and Attitude, Intense Vacuum 18 causes adherence of ePTFE Tubing 10 to Mandrel 9, Splined Mandrel 15 and Edges of Perforations 7 through wall of Mandrel along with Intense Suction, maintain adherence by increasing Purchase, Chaff Scavenge—via dedicated vacuum system 12, Video Imaging System 13 to document conformity with Specs., in real and delayed time frames, as required, Electromagnetic Socket Chuck Lock 5 accurately and firmly holds the Base Cone 6 of each Mandrel which is centered in Conical Socket 22; Position of Mandrel perforations is indexed on base cone attachment—used when creating holes in blood vessel prostheses (FIG. 4A). Vacuum Loss triggers intermittent compensatory "on" cycle to maintain critical adherence. All motion of Compound RIGDA Tooling Assembly 3 and position and attitude of RIGDA tooling 11 are made programmable and micrometer adjustable, "Live Center" 20 butts onto Mandrel tip 8 for additional stabilization as required, and nitrogen gas is used to clean chaff off substrate and cutting surfaces.

In one aspect of the invention, an implantable tube for implantation in a body is provided. Preferably, it is a tube of un-sintered extruded ePTFE having a first surface and a second surface, the tube having any beneficial porosity, the first surface being smooth and the second surface being textured, specifically preferably micro-textured. The second surface has the beneficial effect of inducing bio-integrative scar. The texture and micro-texture is created by the "vibratory and rotary impaling, gouging, distracting, tearing, releasing, avulsing and re-capturing of substrate fragments ("RIGDA tooling") into the thickness dimension of the tubular material, removing the fragments thereof, and leaving behind the finished tubular product. The second surface may have a furrow pattern of highly variably shaped remnant villi with wholly exposed crystalline surfaces, high fluffy regions and low regions of troughs or channels, complex interstices and lowest regions nominally called wells. Optionally, the surface pattern may include plurality of intersecting wells, structure with cross-sectional dimensions of varying width. The pattern may be semi-random or uniform. Patterns, such as furrow patterns, may be repetitive or not, and straight or optionally in a spiral. Optionally, the tube may be a laminated structure.

The second surface is arranged to stimulate a high degree of tissue in-growth, which is preferably defined as in-growth which is at least 15-20 microns deep within the thickness of the micro-texture on test growth at three days in an appropriate laboratory animal model. The second or micro-textured surface is arranged into a complexly configured space which acts to greatly disorder the usually orderly parallel alignment of collagen monomers and, as a consequence, effectively disorganizes scar tissue and softens it to some degree.

The tube thickness may be essentially uniform between the tubular orifices, or may be variable. The diameter of the tube may be uniform or variable. Optionally, the tube wall may be perforated by at least one hole. Additionally or alternatively, the tube may be perforated by numerous slits or lucencies cut into the substrate material by any cutting implement or a laser. The slits or lucencies in the tubular structure manifest as pores or interstices which may contain suffused biologically active material which, in the implanted state, dissolves in biologic fluid as it leaches out of the structure.

A partial short list of surgical uses for a textured ePTFE tube includes: (1) as a body fluid shunt for e.g. cerebrospinal fluid, controlled fistulae and others, (2) as a liner for implants in orthopedic and oral and maxillofacial surgeries to assist in bio-integration, (3) as a structure-conferring tubular implant in reconstructive surgeries of the trachea, external auditory canal, nasal and sinus passages, nasolacrimal duct, and others, (4) as a sling for structures such as catheters, control tubes or wire leads which may require body tissue fixation, (5) as a friction-reduction sleeve around tendons, nerves, and so forth, (6) as coronary artery, vascular and ductal stent grafts, (7) as adhesive repositories for specialized cell populations such as stem cells, drugs, and so forth.

In one implementation, the method for fabrication may be as follows. The tube is mounted onto a hollow mandrel, then mount the mandrel on a hollow spindle on a lathe, wherein a vacuum acts through the hollow mandrel and confers upon the resultant unitary structure a rigid rod-like shape which can be presented to a "RIGDA tooling assembly". The tooling action upon the material causes impaling, gouging, distracting and avulsing of areas of the substrate tubing, leaving behind a tattered and villous substrate surface structure. This complex topology is pristine and crystalline. The convoluted villous substrate surface topology is extremely irregular, with extremely complex adnexal spaces throughout the furrow patterns thus created. Optionally, the heat created through action of the RIGDA tooling may be cooled by liquid Nitrogen spray. The particles of chaff are disposed of preferably by aspiration.

The hollow mandrel is optionally perforated by a large number of generally round perforations through its wall, allowing for intense suction adherence and purchase on the tubular substrate material. The RIGDA tooling process includes some of, or the combined actions of, rotary impaling, gouging, distracting and avulsing, releasing, re-capturing and further avulsing of ePTFE fragments, augmented by the induced vibration inherent in the process as described. Preferably computer control of machine traversal occurs, with the "RIGDA tooling assembly" moving against tubular substrate, or vice versa by moving the mandrel assembly against "RIGDA tooling assembly" or by simultaneous opposing motions of both "tooling" and mandrel assemblies. The methods may include electromagnetically actuated conical and keyed socket chuck enabling accurate centrally aligned tooling and tubing substrate, while permitting a vacuum to act throughout its interior volume. The methods creating of a given texture pattern where multiple "RIGDA tools" are employed simultaneously and where rotary speeds, energy intensities, and micro-texture patterns are highly variable.

Figure 7:
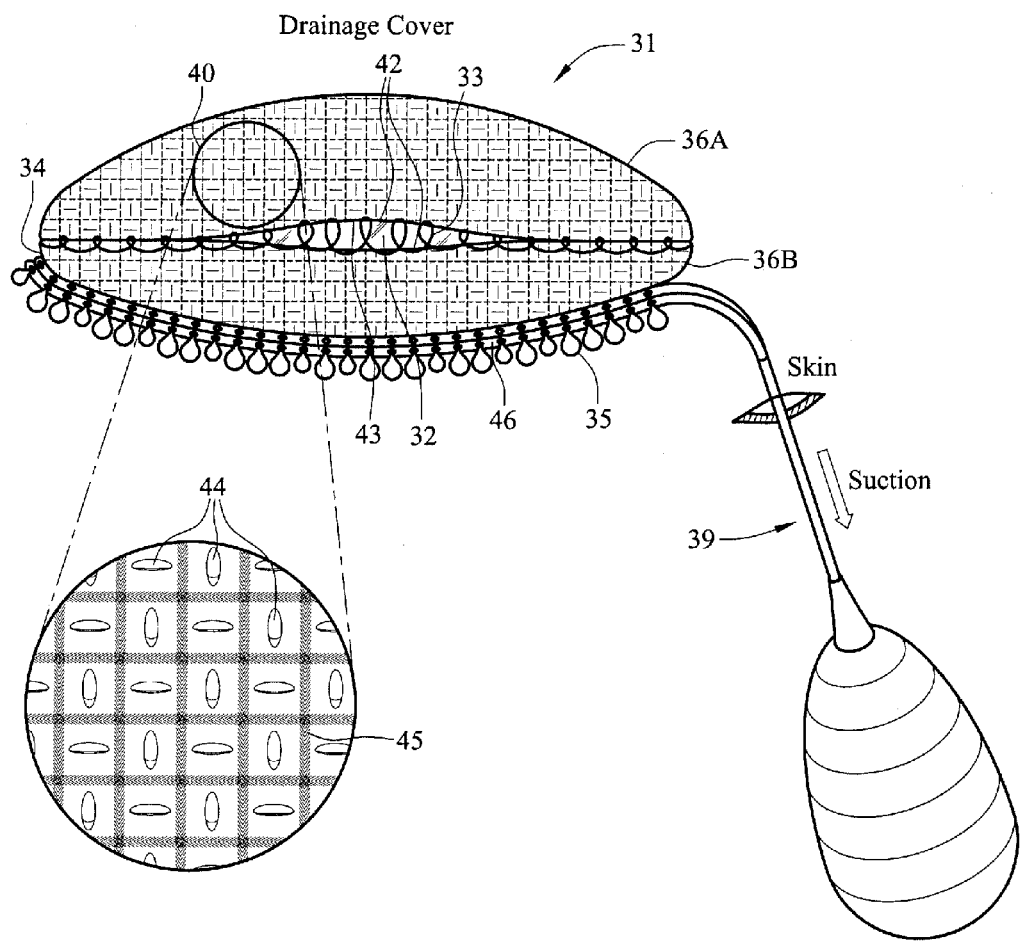
FIG. 7 depicts a custom fitted Drainage Cover surrounding a prototypical breast implant.

The drainage cover is particularly described with reference to FIG. 7. The invented drainage cover 31 in FIG. 7 is shown in a semi-oblique view as if placed on a flat surface, to show its essential enfolding configuration around a prototypical breast implant 32 and with incompletely closed ePTFE ties 33 to show its relation to the enclosed implant.

The drawing depicts the implant 32, reflected bi-lobed cover portions 36A and 36B, ePTFE ties 33, adnexal space 34, interstitial (seroma) fluid 35, texture in grid form 45, oval/slash thru and thru cut lucencies 44 and closed drain system 39. It further shows outward facing aspect 40 of the cover, and it shows perimeters 42 of reflected enveloping portions of the bi-lobed cover 36A and 36B joined to each other at the implant equator by stitching, sewing, or other methods and structures known to those skilled in the art.

The drawing also shows the implant completely enveloped by the drainage cover. The cover is shown with the textured side 40 facing away from the breast implant, and the smooth undersurface of the cover 43 directly facing and contacting the implant. Labeled lucencies 44 and texture pattern 45 are shown in close proximity. The shape and distribution pattern 44 of lucencies are selected to maximize drainage cover performance. A grid pattern represents the applied texture 45, whereas the exemplary ovals/slashes represent the pattern of the lucencies 44 shown. The invented drainage cover 31 enables effective drainage of interstitial fluid from the adnexal space around the implant to the commonly used temporary suction drain 46 which is placed into intimate contact with the cover by the surgeon.

The volume of the space between the cover and the implant (not shown) is a variable factor under the manufacturer's direct control. The surface area of the cover is ideally approximately 12-15% percent larger than the surface area of the implant, which allows for effective intra-operative positioning and post-operative massaging of encapsulating scar.

The multi-lucent and micro-textured ePTFE sheet is positioned between the implant and enveloping soft tissues. The sheet envelopes the implant and is bi-lobed with the opposing perimeters joined by ePTFE ligatures at the equator of the implant. The textured surface faces outward to contact the surrounding soft tissues and the smooth side of the cover makes contact with the implant directly.

The through and through lucencies are configured to allow for ready drainage of the immediate surrounding (adnexal) space when it is under the influence of suction applied to the drainage system. When the skin incision is closed at surgery, the cover is pulled by suction into intimate contact with the surrounding soft tissues and also the implant. Such intimate contact makes it possible for the featured textured surface to induce fibroblasts to grow into and onto the convoluted features of the ePTFE cover thereby beginning the process of bio-integration. The shape and distribution of the through and through lucencies also permits adaptive conformance of the cover to the shape and volume of the implant. Both the pattern and shape of the lucencies may be regular or variable.

Bio-integration of the cover with the soft tissues is complete when the wound has completely healed. The intimate contact between all three elements including breast tissue, cover and implant provides structural support for the entire breast. The timing of non-traumatic removal of the suction drain is dictated by the surgeon's experience. Pleasing shape and softness are thereafter more controllable by the patient under her surgeon's direction.

The drainage cover is optionally formed as follows. It is a thin implantable ePTFE sheet structure, the seroma drainage device preferably having two different surfaces, the first surface being smooth and wherein the second surface features a micro-texture in a pattern. As used throughout, the term 'smooth' relates to a surface having pore sizes, depth and/or diameter of typically less than about 3 microns, and often having pore sizes in the 1 to 2 micron range. As described previously, the micro-texture is preferably comprised of very numerous shredded and torn surface villi, the micro-texture induces bio-integrative scar. The sheet structure also manifests strategically located full thickness lucencies; with the lucencies permitting the flow of biologic fluids through the structure in both directions, and wherein the lucencies permit the sheet to be elongated along any pertinent axis. Thus, the sheet serves as a seroma drainage device in large surgical wounds.

Any beneficial thickness, wherein both surfaces of the sheet structure feature a micro-texture pattern which induces bio-integrative scar, such as where the micro-texture is comprised of very numerous shredded and torn micro-villi, and wherein the full-thickness lucencies permit the flow of biologic fluids through the structure in both directions; and wherein the lucencies permit the sheet to be elongated along any pertinent axis. Preferably the texture is a "micro-texture" which induces scar and serves functionally to bio-integrate with surrounding soft tissue. Preferably, the opposing side is smooth, preventing scar induction or attachment.

When used as a drainage cover for breast implants, the textured side features the micro-texture created using the method generally described herein wherein the sheet is accommodated using a unique mandrel with a large diameter to suit and wherein the opposing side of the sheet is smooth or non-textured. The textured surface of the cover faces away from the implant and toward surrounding soft tissues, and the smooth side of the cover faces toward the implant, yet remains totally un-attached to the implant surface.

Preferably the cover includes through and through cut lucencies to facilitate the sheet stretching along any pertinent axis of elongation, thus permitting adaptive conformance to implant shape and volume. This feature allows for the ingress and egress of biologic fluids into the space between the implant and the cover, thereby enabling good postoperative drainage of seroma fluid over a protracted period of time under the influence of wound suction.

The drainage cover is preferably constructed so that it comprises two lobes of a sheet structure wherein all of the opposing perimeters are joined with filaments of like material under moderate tension, and with the outward facing surface being micro-textured and all of the inward facing surface being substantively smooth or non-textured. The drainage cover may be constructed so that duplicate copies of either or both portions of the corresponding bi-lobed sheet are joined at their corresponding peripheries to enhance the performance of such thicker drainage cover.

The drainage cover may have the texture pattern consisting of parallel or intersecting furrows wherein the cut lucencies are located within the borders of texture furrows. The texture furrows may consist of tattered and shredded surface villi of ePTFE whose function is to induce bio-integrative scar and where the hyper-convoluted micro-topography disorganizes the induced scar.

It will be readily apparent to those of ordinary skill in the art in light of the teachings herein that certain changes and modifications may be made thereto without departing from the spirit or scope of the appended claims. For example, while often described with specific reference to tubes, the texturizing tooling and methods may be used to texturize and structure, such as films, sheets and three dimensional structures. Implantable textured ePTFE tubes and other structures can be engineered to have a wide variety of attributes and functions. Variations of the above-described methods of manufacture of micro-textured tubular ePTFE which are based upon RIGDA tooling and removing of substrate material will be appreciated by those skilled in the art. The salient features of the described sheet-like drainage cover work together to improve upon the prior art. Certain variations and modifications of the preferred embodiment will be apparent to those of ordinary skill in the art. Accordingly, the claims herein should be interpreted as broadly as possible. It is therefore expected that the scope and spirit of the claims in light of the teachings of the invention, be interpreted liberally to include all variations and modifications.

I claim:

1. A method for texturizing an implantable tube for implantation in a body, the tube being an extruded ePTFE tube, the tube having a first inner surface and a second outer surface, the tube having a thickness dimension between the first inner surface and the second outer surface, the second outer surface being textured to promote body tissue bio-integration into the second surface, the second outer surface being textured by the process comprising the steps of:

providing a mandrel sized to receive the inner surface of the tube, the mandrel having a plurality of holes to couple the inner surface of the tube to a vacuum space, releasably affixing the first inner surface to the mandrel by application of a vacuum to the vacuum space, contacting an active rotary gouge to the second outer surface to remove material from the tube, at least including gouging material in the thickness dimension from the second surface toward the first surface, thereby separating the gouged material from the tube, thereby forming an irregularly configured second outer surface, the outer surface having resultant irregular voids, removing the gouged material from the textured second surface, moving the rotary gouge and mandrel relative to one another, and discontinuing application of the vacuum and removing the texturized tube from the mandrel.

2. The method for texturizing an implantable tube of claim 1 wherein the mandrel rotates around an axis of the tube.

3. The method for texturizing an implantable tube of claim 1 wherein the rotary gouge moves parallel to the axis of the tube.

4. The method for texturizing an implantable tube of claim 1 wherein the rotary gouge moves at a non-zero angle relative to the axis of the tube.

5. The method for texturizing an implantable tube of claim 1 wherein multiple active rotary gouges contact the tube.

6. The method for texturizing an implantable tube of claim 1 wherein the mandrel is hollow.

* * * * *